United States Patent
Casavant

(10) Patent No.: US 11,224,752 B2
(45) Date of Patent: Jan. 18, 2022

(54) HIS-BUNDLE PACING CAPTURE VERIFICATION

(71) Applicant: Cardiac Pacemakers, Inc., St. Paul, MN (US)

(72) Inventor: David Arthur Casavant, Reading, MA (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 44 days.

(21) Appl. No.: 16/424,965

(22) Filed: May 29, 2019

(65) Prior Publication Data

US 2020/0009390 A1  Jan. 9, 2020

Related U.S. Application Data

(60) Provisional application No. 62/694,803, filed on Jul. 6, 2018.

(51) Int. Cl.
*A61N 1/37* (2006.01)
*A61B 5/363* (2021.01)

(52) U.S. Cl.
CPC ............ *A61N 1/3712* (2013.01); *A61B 5/363* (2021.01); *A61N 1/3714* (2013.01)

(58) Field of Classification Search
CPC ... A61N 1/3712; A61N 1/3714; A61B 5/0464
See application file for complete search history.

(56) References Cited

U.S. PATENT DOCUMENTS

| | | | |
|---|---|---|---|
| 8,565,880 B2 | 10/2013 | Dong et al. | |
| 8,588,907 B2 | 11/2013 | Arcot-Krishnamurthy et al. | |
| 9,168,382 B2 | 10/2015 | Shuros et al. | |
| 2004/0034390 A1* | 2/2004 | Casavant | A61N 1/3622 607/9 |
| 2006/0241710 A1* | 10/2006 | Rueter | A61N 1/3712 607/28 |
| 2011/0264158 A1* | 10/2011 | Dong | A61B 5/7264 607/9 |
| 2012/0239106 A1* | 9/2012 | Maskara | A61N 1/371 607/28 |
| 2013/0261685 A1* | 10/2013 | Shuros | A61N 1/39622 607/4 |
| 2019/0134405 A1* | 5/2019 | Sheldon | A61B 5/361 |

* cited by examiner

*Primary Examiner* — Ankit D Tejani
*Assistant Examiner* — Joshua Brendon Solomon
(74) *Attorney, Agent, or Firm* — Schwegman Lundberg & Woessner, P.A.

(57) ABSTRACT

Systems and methods for pacing cardiac conductive tissue are described. In an embodiment, a medical system includes an electrostimulation circuit to generate His-bundle pacing (HBP) pulses. A sensing circuit senses an atrial activation. A control circuit detects a retrograde atrial conduction timing, such as a His-to-atrial interval between the HBP pulse and the sensed atrial activation in response to the HBP pulse, and verifies capture status using the determined retrograded atrial conduction timing. Based on the capture status, the control circuit determines a HBP threshold, and the electrostimulation circuit delivers HBP pulses in accordance with the determined HBP threshold.

20 Claims, 5 Drawing Sheets

HIS-BUNDLE PACING CAPTURE VERIFICATION

CLAIM OF PRIORITY

This application claims the benefit of priority under 35 U.S.C. § 119(e) of U.S. Provisional Patent Application Ser. No. 62/694,803, filed on Jul. 6, 2018, which is herein incorporated by reference in its entirety.

TECHNICAL FIELD

This document relates generally to medical systems, and more particularly, to systems, devices and methods for pacing of cardiac conductive tissue, such as a His bundle.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, which propagate through natural electrical conduction pathways known as His-Purkinje system to various regions of the heart to excite the myocardial tissue of the heart. For example, the action potentials originated from the SA node propagate through the atrioventricular (AV) node, the His bundle (also known as Bundle of His), the bundle branches, and Purkinje fibers to reach the ventricular myocardium, resulting in coordinated contractions in both ventricles.

Coordinated delays in the propagation of the action potentials in a normal electrical conduction system cause the various portions of the heart to contract in synchrony to result in efficient pumping functions. A blocked or otherwise abnormal electrical conduction and/or deteriorated myocardium may cause dyssynchronous contraction of the heart, resulting in poor hemodynamic performance, including a diminished blood supply to the heart and the rest of the body. For example, an abnormal delay in the transmission of the action potentials in the His bundle can cause irregular or dyssynchronous contractions of the ventricles, resulting in an abnormal rhythm of the heart.

Artificial cardiac pacing system have been used to rectify cardiac dyssynchrony and to improve hemodynamic performance. The artificial cardiac pacing system can provide electrical stimulations to one or more portions of the heart such as to restore normal functioning of the heart to a certain extent. For example, right ventricular pacing via electrodes implanted in the apex of the RV have been used in both single ventricular and biventricular (BiV) pacing. RV apex pacing directly excites the ventricular myocardium, rather than propagating the action potentials through the natural conduction pathways. Studies have shown that, in some patients, long-term RV apex pacing may result in loss of synchronous mechanical contraction of RV and LV, partially due to the interventricular delay in impulse propagation to the left ventricle. Consequently, permanent changes in myocardial perfusion and structure may develop over time in these patients, which may further decrease cardiac output and deteriorate ventricular function. BiV pacing involves RV pacing via one lead, and LV pacing via another lead, and has been demonstrated to restore synchronized contraction of both ventricles. However, the potential adverse impact on ventricular function produced by the RV apex pacing may still exist in BiV pacing. Additionally, compared to cardiac depolarization through AV node activation and propagation through the natural conduction pathways, the BiV pacing may not produce similarly coordinated cardiac contractions. Moreover, the surgical procedure for placing the LV lead through the coronary sinus and into a vein on the left ventricular wall can be complex and challenging in some patients.

OVERVIEW

Hemodynamic response to artificial pacing can depend on many factors, including pacing site selection and pacing configurations. Many patients receiving artificial pacing therapy have an intact His bundle and the natural cardiac electrical conduction system in the ventricles, and therefore having normal ventricular activation. Conventional cardiac pacing such as long-term RV apex pacing may cause a decrease in cardiac efficiency due to the uncoordinated contraction sequence, and eventually exhibit adverse long-term effects. Dyssynchronous contraction of the ventricles occurs during conventional right ventricular pacing because the activation sequence can be much slower and propagate slowly from the right to the left ventricle across the interventricular septum, thereby causing ventricular dyssynchrony. This sequence of activation results in an uncoordinated contraction which does not occur during biventricular activation through the natural conduction system of the heart. The cells of the natural conduction system can propagate an activation signal about four times faster than working myocardium. A cardiac rhythm or functional management device configured to pace the His bundle is an alternative to conventional ventricular pacing in some patients. His-bundle pacing (HBP) may activate the heart's natural His-Purkinje system in some patients, and produce efficient and coordinated cardiac contractions. The potentially long-term harmful hemodynamic effects that may occur from continuous RV apex pacing may also be eliminated or reduced.

However, when not being successful, the HBP may not adequately restore cardiac synchrony. In some instances, the electrical stimulation pulse may lose its ability to activate (or capture) the His bundle, but only activates the para-Hisian myocardium surrounding the His bundle. Stimulating muscles near the His bundle may cause dyssynchronous patterns similar to RV apical pacing. This undesirable effect is referred to as para-Hisian capture. Simultaneous capture of the His bundle and para-Hisian muscle (also known as a non-selective His-bundle capture) can be as clinically effective as the His-bundle only capture absent of para-Hisian muscle capture (also known as a selective His-bundle capture). This is because the ventricles are activated predominately by the rapidly conducting natural conduction system. Another undesirable effect of HBP is known as a complete loss of capture (LOC), where the HBP pulses capture neither the para-Hisian myocardium nor the His bundle. Verification of His-bundle capture status can be important functions of a HBP device in monitoring and assessing HBP therapy efficacy.

Conventionally, capture status verification techniques have relied upon evoked response detection that is muscular in origin. Measuring the evoked His bundle depolarization during HBP represents an technical challenge. For example, the evoked His-bundle depolarization may have a relatively small amplitude and very short in duration, and is overwhelmed by post-pacing polarization effect introduced by the HBP pulses. Additionally, because some patients receiving HBP therapy often have various degrees of heart block, and the electrodes for sensing the evoked His-bundle response may be positioned in close proximity to atrial myocardium, the sensed evoked His-bundle response may be confounded by atrial activation. As such, programming the His-bundle sense channel to a high sensitivity in order to sense an evoked response may introduce the risk of over-sensing of atrial activity. In some cases, the over-sensing of atrial activity may inappropriately inhibit the HBP therapy, and lead to critical consequences particularly in patients with heart block, and who are pacemaker-dependent.

HBP capture verification can be based on a detection of presence or absence of conducted ventricular activation, such as R-wave sensed from an ECG. However, for patients varying degrees of heart block or sick sinus syndrome, an atrial-Hisian (AH) pacing mode is typically used to deliver HBP. The HBP pulses may be delivered only when intrinsic atrial activation (As), or atrial pacing (Ap), fails to produce propagatable depolarization of the AV node and the His bundle. As there is generally no RV lead or ventricular sensing electrode, HBP capture verification based on R-wave or ventricular activation detection may not be a feasible option for patients receiving AH mode HBP.

The capture status verification may also help determine an individualized HBP threshold. The HBP threshold represents minimal energy required to excite the His bundle and to correct the cardiac conduction abnormality. Typically, to ensure effective capture, pacing output may be set to the pacing threshold plus a safety margin. The HBP threshold may be different from person to person, and may vary over time in a patient due to changes in patient pathophysiology (e.g., development of a new medical condition such as myocardial ischemia, fibrotic scarring, or progression of an existing medical condition), medication, or lead migration, dislodgment, or micro-dislodgment, among other causes. Determining pacing threshold and tracking changes of that threshold over time in a patient can be beneficial to titrate individualized electrostimulation therapy to achieve desired patient outcome.

For at least the above reasons, the present inventor has recognized that there is an unmet need for an artificial pacing system that can more effectively detect His-bundle capture status, automatically determine or adjust individualized HBP threshold, and to more therapy efficacy in response to HBP delivered in accordance with the individualized HBP threshold. Embodiments of the present subject matter provide systems, devices, and methods to improve HBP therapy efficacy. An exemplary medical system includes circuitry for generating HBP pulses to stimulate a His bundle of the heart, and detecting an atrial activation of the heart. A control circuit may detect a retrograde atrial conduction using the sensed atrial activation, and verify His-bundle capture status using timing of the retrograde atrial conduction. The time for retrograde atrial conduction along a pathway that solely encompasses the atrioventricular node is usually on the order of 100 msec. In the absence of His-bundle capture, a substantially longer HBP to atrial conduction time may occur, as the HBP pulses typically slowly conduct down the intraventricular system and the Purkinje fiber, through the His bundle, then up through the atrioventricular node to reach the right atrium. Therefore, His-bundle capture status may be determined by monitoring retrograde atrial activation time. HBP pulses may be delivered under a number of stimulation strength values, and a HBP threshold may be determined based on the capture status under different stimulation strength values. The electrostimulation circuit may deliver HBP pulses in accordance with the determined HBP threshold.

Example 1 is a system for pacing a heart. The system comprise an electrostimulation circuit configured to generate His-bundle pacing (HBP) pulses to stimulate a His bundle of the heart, a sensing circuit configured to sense an atrial activation of the heart, and a control circuit including a capture verification circuit configured to detect a retrograde atrial conduction using timing of the sensed atrial activation in response to the stimulation of the His bundle, and to verify a His-bundle capture status based at least on the detected retrograde atrial conduction.

In Example 2, the subject matter of Example 1 optionally includes the sensing circuit that may be configured to sense the atrial activation during an atrial detection window (WHA) following the HBP pulse. The capture verification circuit may be configured to verify the His-bundle capture status as one of a His-bundle capture if the atrial activation is detected within the WHA, or a para-Hisian capture or a loss of capture if no atrial activation is detected within the WHA.

In Example 3, the subject matter of any one or more of Examples 1-2 optionally includes the control circuit that may be configured to determine retrograde conduction timing including a His-to-atrial interval (HAI) between a HBP pulse and the sensed atrial activation in response to the HBP pulse.

In Example 4, the subject matter of Example 3 optionally includes the capture verification circuit that may be configured to verify the His-bundle capture status as one of a His-bundle capture if the determined HAI falls below a threshold value, or a para-Hisian capture or a loss of capture if the determined HAI exceeds the threshold value.

In Example 5, the subject matter of Example 4 optionally includes the capture verification circuit that may be configured to generate the threshold value using a central tendency of a plurality of HAIs falling within a specific range in response to HBP pulses.

In Example 6, the subject matter of any one or more of Examples 3-5 optionally includes the control circuit that may include a pacing threshold test circuit coupled to the capture verification circuit. The capture verification circuit may be configured to verify His-bundle capture status in response to HBP pulses having multiple stimulation strength values in accordance with a threshold test protocol, and the pacing threshold test circuit may be configured to determine, using the verified capture status, an HBP threshold.

In Example 7, the subject matter of Example 6 optionally includes the threshold test protocol that may include a stimulation strength ramp-down protocol, and the pacing threshold test circuit may be configured to determine the HBP threshold corresponding to a prolongation of HAI exceeding a threshold.

In Example 8, the subject matter of Example 6 optionally includes the threshold test protocol that may include a stimulation strength ramp-up protocol, and the pacing threshold test circuit may be configured to determine the HBP threshold corresponding to a shortening of HAI falling below a threshold.

In Example 9, the subject matter of any one or more of Examples 6-8 optionally includes the pacing threshold test circuit that may be configured to determine or update the HBP threshold in response to a trigger event.

In Example 10, the subject matter of Example 9 optionally includes the trigger event that may include a para-Hisian capture or a loss of capture.

In Example 11, the subject matter of Example 9 optionally includes the trigger event that may include a user command.

In Example 12, the subject matter of any one or more of Examples 1-11 optionally includes an arrhythmia detector that may be configured to detect a presence or absence of atrial tachyarrhythmia. The capture verification circuit may be configured to verify a His-bundle capture status in the absence of the atrial tachyarrhythmia.

In Example 13, the subject matter of Example 12 optionally includes the pacing threshold test circuit that may be configured to determine the HBP threshold in response in the absence of the atrial tachyarrhythmia.

In Example 14, the subject matter of any one or more of Examples 3-13 optionally includes the control circuit that may be configured to generate a trend of HAI over time using HAIs corresponding to a plurality of HBP pulses.

In Example 15, the subject matter of Example 14 optionally includes the control circuit that may be configured adjust a stimulation parameter of HBP based on the verified His-bundle capture status.

Example 16 is a method for operating a pacing system to stimulate a heart. The method comprises steps of: generating His-bundle pacing (HBP) pulses to stimulate a His bundle of the heart using an electrostimulation circuit; sensing an atrial activation of the heart using sensing circuit; detecting, via a control circuit, a retrograde atrial conduction using timing of the sensed atrial activation in response to the stimulation of the His bundle; and verifying, via the control circuit, a capture status based at least on the detected retrograde atrial conduction.

In Example 17, the subject matter of Example 16 optionally includes steps of: sensing the atrial activation during an atrial detection window (WHA) following the HBP pulse, and verifying the capture status includes recognizing a His-bundle capture if the atrial activation is detected within the WHA, or a para-Hisian capture or a loss of capture if no atrial activation is detected within the WHA.

In Example 18, the subject matter of any one or more of Examples 16-17 optionally includes measuring a His-to-atrial interval (HAI) between a HBP pulse and the sensed atrial activation in response to the HBP pulse. The verifying the capture status includes recognizing a His-bundle capture if the determined HAI falls below a threshold value, or a para-Hisian capture or a loss of capture if the determined HAI exceeds the threshold value.

In Example 19, the subject matter of Example 18 optionally includes steps of varying stimulation strength of the HBP pulses and verifying His-bundle capture status in response to HBP under the varied stimulation strength, and determining a HBP threshold using the verified His-bundle capture status under the varied stimulation strength.

In Example 20, the subject matter of Example 19 optionally includes steps of varying the stimulation strength of the HBP pulses including ramping down the stimulation strength, and determining the HBP threshold corresponds to a prolongation of HAI exceeding a threshold.

In Example 21, the subject matter of any one or more of Examples 19-20 optionally includes steps of varying the stimulation strength of the HBP pulses including ramping up the stimulation strength; and determining the HBP threshold corresponds to a shortening of HAI falling below a threshold.

In Example 22, the subject matter of any one or more of Examples 18-21 optionally includes generating a trend of HAI over time using HAIs corresponding to a plurality of HBP pulses.

In Example 23, the subject matter of any one or more of Examples 16-22 optionally includes detecting a presence or absence of atrial tachyarrhythmia. The verification of the capture status may be performed in the absence of the detection of atrial tachyarrhythmia.

The systems, devices, and methods discussed in this document may improve the technology of cardiac pacing in patients with cardiac disease, such as heart failure. HBP may activate natural His-Purkinje system, thereby preserving ventricular synchrony and improving cardiac performance without structural and functional impairment to the heart. A technological challenge in HBP is to verify His-bundle capture status, and determine appropriate, individualized HBP threshold to ensure reliable activation of the His-Purkinje system. While a high stimulation output may more likely to produce His-bundle capture, it consumes more battery power, and may have side effects in some patients, such as phrenic nerve stimulation, pain sensation, among others. The present subject matter improves automated His-bundle capture verification and individualized HBP threshold test, with little to no additional cost or system complexity. The His-bundle pacing as discussed in the present document leverages the electrophysiology of the His bundle region, and improves pacing efficiency utilizing the natural conduction mechanisms of the heart, while reducing long-term harmful hemodynamic effects associated with RV apex pacing. A embodiment of the His-bundle capture verification discussed herein is based on retrograde atrial conduction, such that no ventricular lead (e.g., an RV lead) or ventricular sensing electrodes are required to sense ventricular response to HBP. This can be advantageous especially for patients who do not have an RV sensing lead, such as patients receiving an AH mode HBP. With improved synchrony and cardiac performance, fewer unnecessary medical interventions, such as drugs, procedures, or device therapies, may be scheduled, prescribed, or provided to such patients. As a result, overall system cost savings may be realized.

The His-bundle capture verification based on retrograde atrial conduction timing and the individualized pacing threshold testing as discussed in this document may also improve the functionality of a cardiac pacing system or device. Device memory usage may be more efficient by storing HBP thresholds that are clinically more relevant to titrating cardiac pacing therapy to improve therapy efficacy. Automatic HB capture verification and threshold monitoring algorithms may also facilitate remote patient monitoring. The HBP threshold as determined using the capture verification based on the retrograde atrial conduction timing may not only improve effectiveness of HBP therapy, but may extend battery life and implantable device longevity as well with reduced pacing energy and avoidance of unnecessary device therapies. Additionally, device size may be reduced to achieve existing performance metrics.

While His-bundle pacing is specifically discussed in this document, this is meant only by way of example and not limitation. It is within the contemplation of the inventor, and within the scope of this document, that the systems, devices, and methods discussed herein may be applied to stimulate other conductive cardiac tissue, such as the right or left bundle branches or fascicles, or the Purkinje fibers.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for pacing cardiac conductive tissue. An embodiment of the system may include an electrostimulator to generate His-bundle pacing (HBP) pulses to stimulate a His bundle. The system may sense an atrial activation, determine retrograde atrial conduction timing such as a His-to-atrial interval in response to HBP delivery, and verify His-bundle capture status using the determined retrograde atrial conduction timing. The system may determine a HBP threshold based on the capture status under different HBP stimulation strength values. The electrostimulator may deliver HBP pulses in accordance with the determined HBP threshold.

Figure 1:
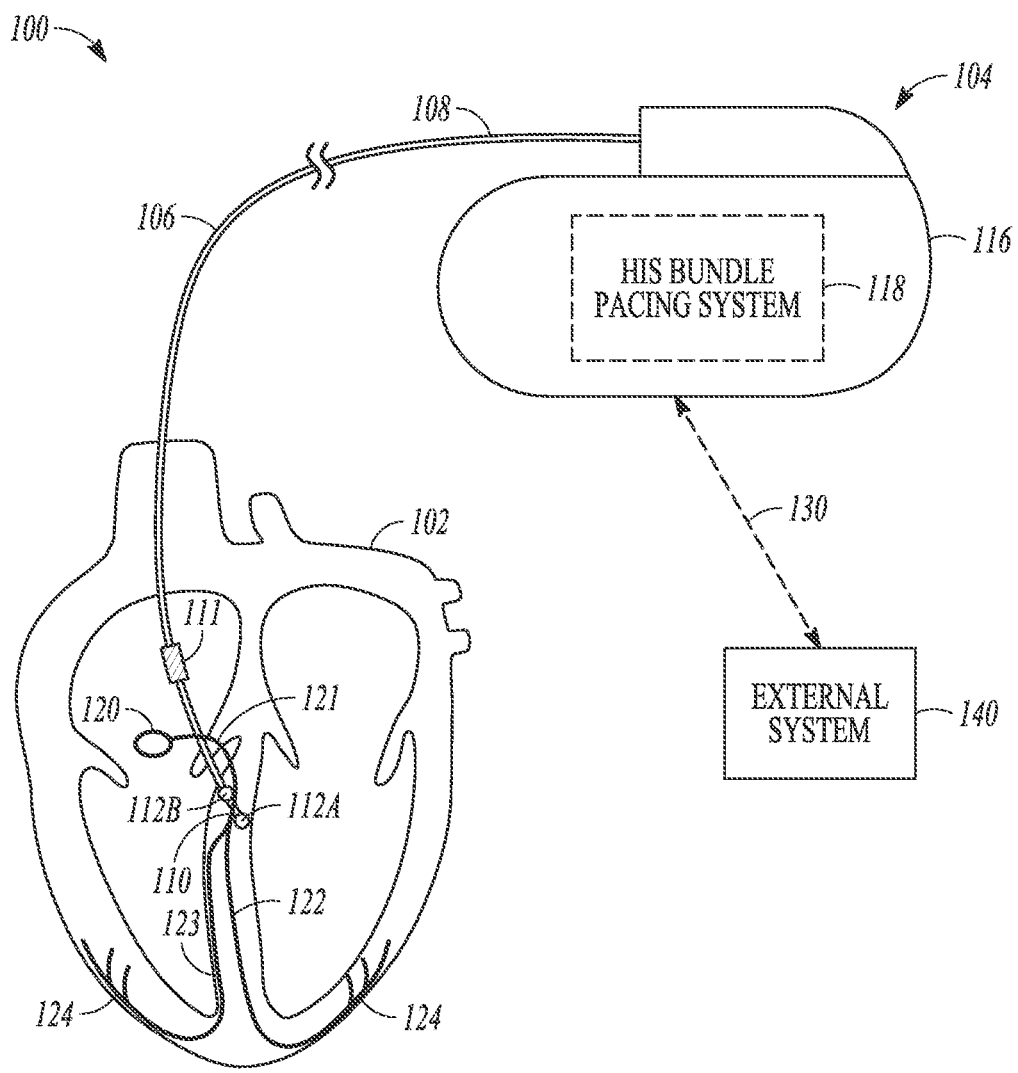
FIG. 1 illustrates generally an example of a cardiac disease management system and portions of an environment in which the system may operate.

FIG. 1 is a schematic diagram illustrating an embodiment of a cardiac disease management system 100 and portions of an environment in which the system 100 may operate. The cardiac disease management system 100 may perform a range of activities, including remote patient monitoring, diagnosis of a disease condition, and providing a therapy to treat the disease condition and to improve patient outcome. In an example, the therapy may include His-bundle pacing (HBP). One or more of these activities may be performed proximal to a patient (e.g., in the patient's home or office), through a centralized server (e.g., in a hospital, clinic or physician's office), or through a remote workstation (e.g., a secure mobile computing device).

As illustrated in FIG. 1, the cardiac disease management system 100 may be coupled to a patient's heart 102. The cardiac disease management system 100 includes an ambulatory medical device (AMD) and a lead system, configured to treat one or more cardiac diseases, such as cardiac arrhythmias or heart failure. The AMD may be an implantable device subcutaneously implanted in a chest, abdomen, or other parts of the patient, a subcutaneous monitor or diagnostic device, or a wearable medical device such as a patch-based device or a smart wearable or accessory, among others. In the example as illustrated in FIG. 1, the AMD includes an implantable medical device (IMD) 104. Examples of the IMD 104 may include a pacemaker, a pacemaker/defibrillator, a cardiac resynchronization therapy (CRT) device, a cardiac remodeling control therapy device, a neuromodulator, a drug delivery device, a biological therapy device, or an implantable diagnostic device such as a cardiac monitor or a loop recorder, among other implantable devices.

The lead system may include one or more transvenously, subcutaneously, or non-invasively placed leads or catheters. Each lead or catheter may include one or more electrodes. The arrangements and uses of the lead system and the associated electrodes may be determined by patient need and capability of the IMD 104. The associated electrodes on the lead system may be positioned at the patient's thorax or abdomen to sense a physiological signal indicative of cardiac activity, or a physiological response to stimulation of a target tissue. The lead system may be surgically inserted into, or positioned on the surface of, a heart 102. The electrodes associated with the lead system may be disposed in a target site in a right atrium (RA), a right ventricle (RV), a left atrium (LA), or a left ventricle (LV), or other body parts. Stimulation energy may be delivered to a target site via one or more of these electrodes. Some electrodes may be used for sensing cardiac activity, such as an intrinsic or evoked cardiac electrical activity.

In the illustrated example, the lead system may include a lead 106 having a proximal end 108 configured to be connected to the IMD 104, and a distal end 110 that includes one or more electrodes configured to deliver stimulation energy, such as in a form of pacing pulses, to the His bundle 121. FIG. 1 illustrates, by way of example and not limitation, two electrodes including a tip electrode 112A and a ring electrode 112B. Additional electrodes may be included in the lead 106 for sensing electrical activity or for delivering stimulation energy. The lead 106 may be placed such that one or more electrodes, such as 112A-112B, are positioned in or on a His bundle 121, a region distal to the blocked or slowly conducting AV node and in the AV septum, an interventricular septum region, or a right atrial region near the His-bundle 121. As part of the natural electrical conduction system of the heart 102, the His bundle 121 transmits the electrical impulses from the AV node 120 to the point of the apex of the fascicular branches via the left bundle branch 122 and the right bundle branch 123. Each of the left and right branch bundles leads to the Purkinje fibers 124, which provide electrical conduction to the ventricles, causing the ventricles to contract. In some examples, the lead 106 may be placed such that one or more electrodes associated with the lead 106, such as 112A-112B, are positioned at or near other parts of the natural conduction pathways, such as one of the bundle branches 122 or 123, the Purkinje fibers 124, or other conductive tissue, in addition to or in lieu of a region at or near the His bundle 121.

In an example, the lead 106 may be a single pass lead having a plurality electrodes for stimulating multiple cardiac sites, including electrodes disposed at or near the His bundle (e.g., the electrodes 112A-112B) and electrodes disposed in one or more of RA, RV, LA, or LV of the heart 102. In some examples, in addition to the lead 106, the lead system may include separate leads for placement in different heart chambers or sites, such as an RA lead having one or more RA electrodes to stimulate a portion of RA or to sense RA electrical activity, a RV lead having one or more RV electrodes to stimulate a portion of RV or to sense RV electrical activity, or an LV lead having one or more LV electrodes to stimulate a portion of LV or to sense LV activity. As to be discussed in the following, the cardiac disease management system 100 may deliver His-bundle pacing (HBP) and sense retrograde atrial activation to verify whether the HBP captures the His-bundle. In an example, the lead 106 has only electrodes positioned in an atrium (e.g., RA), without an electrode in a ventricular (e.g., RV or LV). In some examples, the cardiac disease management system 100 may include one or more leadless stimulators/sensors untethered to a lead and in wireless communication with the IMD 104. The leadless stimulators/sensors may deliver electrostimulation, sense a physiological signal, such as cardiac electrical signals in response to cardiac stimulation, and transmit the sensed data to the IMD 104.

The IMD 104 may include a hermetically sealed housing 116 that houses one or more of an electrostimulation circuit, a sensing circuit, a control circuit, a communication circuit, and a battery, among other components. In an example, the IMD 104 includes a His-bundle pacing system 118 configured to generate His-bundle pacing (HBP) pulses to stimulate the His bundle 121, such as via the lead 106 and the associated electrodes 112A or 112B. The His-bundle pacing system 118 may be programmed to deliver unipolar His-bundle pacing, where the pacing energy (current or voltage) is applied between one of the electrodes 112A-112B (e.g., as a cathode) and the housing 116 (e.g., as an anode). Alternatively, the His-bundle pacing system 118 may be programmed to deliver bipolar His-bundle pacing, where the pacing energy (current or voltage) is applied between two electrodes positioned at or near the His bundle, such as between the electrodes 112A and 112B. In some examples, electrodes used for unipolar or multipolar (e.g., bipolar or quadripolar) His-bundle pacing may be selected by a system user from a plurality of candidate electrodes from a given lead or multiple separate leads comprising the pacing system, and programmed into the His-bundle pacing system 118. In some examples, HBP pulses may be provide by a leadless device, such as a leadless cardiac pacemakers (LCP). One or more electrodes may be distributed on the body of the LCP and in contact with His-bundle region to deliver the HBP pulses.

The His-bundle pacing system 118 may sense a physiological signal using one or more electrodes associated with the lead system or a physiological sensor. Examples of the physiological signal may include an electrocardiogram (ECG), an intracardiac electrogram (EGM) such as an atrial EGM, a ventricular EGM, or a His bundle EGM, an thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, an intracardiac acceleration signal, a respiration signal, or a physical activity or exertion level signal, among others. In an example, the His-bundle pacing system 118 may sense an atrial activation signal using one or more electrodes or physiologic sensors. The atrial activation may be in response to HBP delivery. In an example, the atrial activation signal may include an intra-atrial EGM via an electrode positioned within or on the epicardial surface of the left or right atrium, such as an atrial electrode 111 associated with the lead 106 and positioned in the RA to sense an atrial EGM therefrom. Additionally or alternatively, the intra-atrial EGM may be sensed using an electrode on a dedicated atrial lead, such as an RA lead or an LA lead, as discussed above. In another example, the atrial activation information may be extracted from a surface ECG, such as represented by the P-waves on an ECG signal. In yet another example, the atrial activation signal may include sensor signals indicative of atrial mechanical contraction. Examples of atrial mechanical signal may include impedance signal, heart sounds signal, or cardiac pressure signals, among others.

The His-bundle pacing system 118 may detect retrograde atrial conduction using the sensed atrial activation. Retrograde atrial conduction refers to the conduction of the activation wavefront from the His bundle site of pacing (or a ventricular site or AV node) into and through the atria such as via accessory pathways. The retrograde atrial activation (e.g., P waves) follows ventricular depolarization, such that the patient is not in AV synchrony and has lost the benefits of atrial kick during a cardiac cycle. Since many patients receiving HBP therapy have intact atrio-ventricular conduction, when HBP pulses are delivered at a rate faster than the sinus rate (e.g., 10-20 bpm higher) and capture the His bundle, the depolarization wavefront may propagate back to atria, causing retrograde atrial activation. Therefore, monitoring the retrograde atrial conduction timing such that it occurs with an expected electrophysiologic range, such as 100-225 milliseconds (msec) in an example, may help verify His-bundle capture.

The retrograde atrial conduction typically occurs within a short time interval following the HBP pulse before the next cardiac cycle commences. The His-bundle pacing system 118 may determine timing of the retrograde atrial conduction, such as a His-to-atrial interval (HAI) between a HBP pulse and the sensed atrial activation in response to the HBP pulse. A His-bundle capture status may be verified based at least on the retrograde atrial conduction timing. In accordance with the His-bundle capture status, the His-bundle pacing system 118 may adjust one or more pacing parameters, such as increasing the pacing amplitude to improve His-bundle capture. The His-bundle pacing system 118 may additionally determine a HBP threshold representing a HBP strength threshold capable of capturing the His bundle. The His-bundle pacing system 118 may deliver HBP pulses according to the determined HBP threshold. Examples of His-bundle capture verification based on retrograde atrial conduction and HBP threshold test are discussed below, such as with reference to FIGS. 2-4.

The IMD 104 may communicate with an external system 140 via a communication link 130. The external system 140 may include a dedicated hardware/software system such as a programmer, a remote server-based patient management system, or alternatively a system defined predominantly by software running on a standard personal computer. The external system 140 may include a proximal external device such as a programmer device in proximity of the IMD 104. A clinician may manage the patient 102 through the IMD 104 via the communication link 130. This may include, for example, programming the IMD 104 to sense physiological signals, analyzing the physiological signals to detect a medical condition such as heart failure, assessing therapy efficacy, performing a self-diagnostic test, or initiating or adjusting a therapy such as HBP. Additionally, the external system 140 may receive device data from the IMD 104 via the communication link 130. Examples of the device data may include real-time or stored physiological signals collected from the patient 102, physiological response to therapies delivered to the patient 102, or device operational status of the IMD 104 (e.g., battery status and lead impedance). The communication link 130 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

The external system 140 may monitor patient condition and the function of IMD 104. In various embodiments, the external system 140 may include a user interface to display received information to the user, and receive user input for operation control of the IMD 104. In an example, the external system 140 may be configured to verify pacing capture status, perform pacing threshold test to determine a HBP threshold. The capture verification and threshold testing may be executed periodically, or triggered by a specific event such as a user command. A user may use the external system 140 to program the IMD 104, such as to configure a pacing vector (e.g., specifying anode and cathode electrodes) to deliver HBP, or to configure a sense vector to sense a physiological signal.

The external system 140 may include a remote device in a location relatively distant from the IMD 104 and in communication with the proximal external device via a telecommunication network. The remote device can evaluate collected patient data and provide alert notifications, among other possible functions. In an example, the remote device may include a centralized server acting as a central hub for collected patient data storage and analysis. The server may be configured as a uni-, multi- or distributed computing and processing system. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the IMD 104. By way of example, alert notifications may include a Web page update, phone or pager call, E-mail, SMS, text or "Instant" message, as well as a message to the patient and a simultaneous direct notification to emergency services and to the clinician. Other alert notifications are possible. In various examples, the remote device may additionally include one or more locally configured clients or remote clients securely connected over the telecommunication network to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The external system 140 may output the detected medical events or therapy efficacy information (such as capture verification or classification) to a system user such as the patient or a clinician, or to a process including, for example, an instance of a computer program executable in a microprocessor. In an example, the process may include an automated generation of recommendations for initiating or titrating a medical therapy or an electrostimulation therapy. In an example, the external device 120 or the remote device 124 may include a respective display unit for displaying the physiological signals, stimulation parameters, capture verification, or classification of capture types, among other intermediate analyses and computations. Alerts, alarms, emergency calls, or other forms of warnings to signal the detected medical event may also be generated.

Portions of the IMD 104 or the external system 140 may be implemented using hardware, software, firmware, or combinations thereof. Portions of the IMD 104 or the external system 140 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
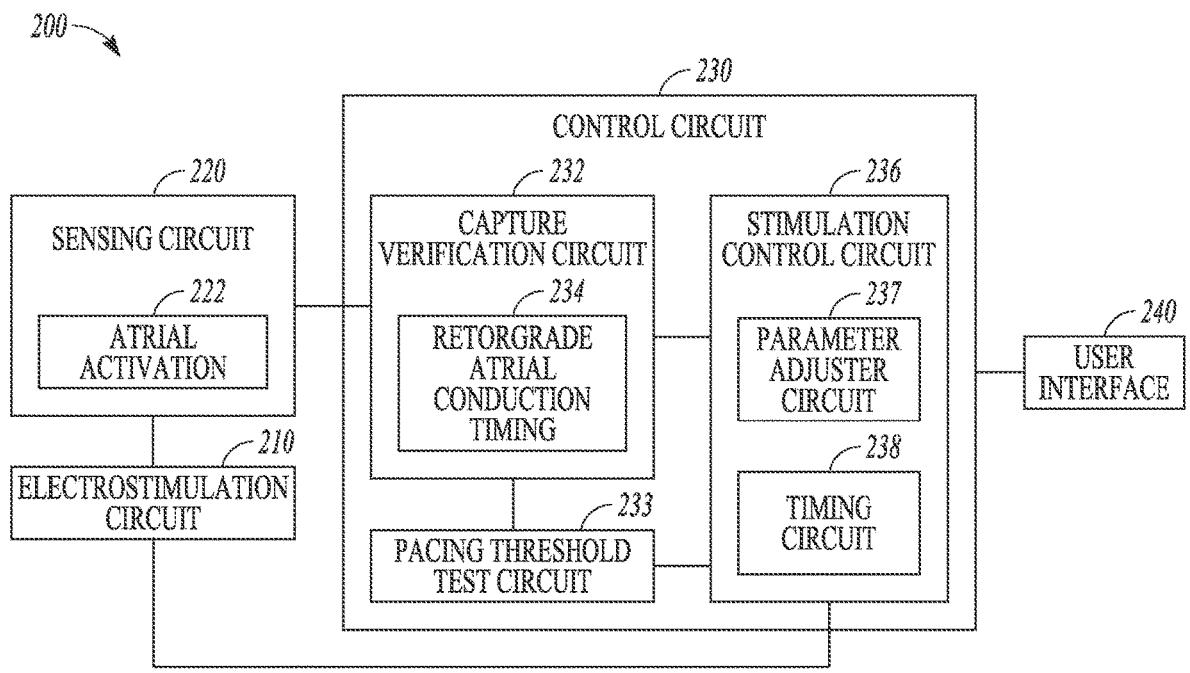
FIG. 2 is a block diagram illustrating an example of portions of a His-bundle pacing system.

FIG. 2 is a block diagram illustrating an embodiment of portions of a His-bundle pacing system 200. The His-bundle pacing system 200 represents an embodiment of the His-bundle pacing system 118, and may include an electrostimulation circuit 210, a sensing circuit 220, a control circuit 230, and a user interface 240.

The electrostimulation circuit 210 may be configured to generate stimulation energy for delivery to the heart 102, such as via one or more leads and the associated electrodes. The electrostimulation circuit 210 may be configured to generate His-bundle pacing (HBP) pulses for delivery to a target pacing site at or near the His bundle such as via the lead 106 and one or more of the electrodes 112A-112B. The target site may include an interventricular septum region or a right atrial region near the His-bundle, or other conductive tissue such as right or left bundle branches or fascicles, or Purkinje fibers. In an example, the HBP pulses may be delivered in multiple cardiac cycles, such that at least one pulse is delivered within each of the multiple cardiac cycles. In various examples, the electrostimulation circuit 210 may additionally generate electrostimulation to stimulate non-cardiac tissue, such as nerve tissue, muscle tissue, or other excitable tissue.

The electrostimulation circuit 210 may generate HBP pulses according to one or more stimulation parameters, such as provided by control circuit 230. Examples of the stimulation parameters may include information about stimulation site, stimulation strength, stimulation mode, or stimulation timing, among other parameters. Stimulation site includes information about pacing site, pacing vector configuration (e.g., anode and cathode electrodes), unipolar or bipolar pacing, cardiac resynchronization therapy (CRT), BiV pacing, or synchronized left ventricle (LV)-only pacing, single site pacing of only one site of a heart chamber (e.g., the left ventricle), or multisite pacing (MSP) of two or more sites of a heart chamber within the same cardiac cycle, among others. Stimulation strength parameters determine the amount of energy delivered to the pacing site, and may include pulse amplitude, pulse width, pulse frequency, pulse waveform, duty cycle, or stimulation duration.

Stimulation mode includes, by way of example and not limitation, a His-bundle only mode, an atrial-Hisian (AH) pacing mode, a His-ventricular (HV) pacing mode, or an atrial-His-ventricular (AHV) pacing mode. In the His-bundle only pacing mode, atrial activation may be sensed by the His-bundle pacing electrode, such as by using a single pass lead, or a leadless pacemaker having a form factor with multiple electrodes positioned such that reliable atrial sensing may be achieved. In the AH pacing mode, the HBP pulses may be delivered only when intrinsic atrial activation (As), or atrial pacing (Ap), fails to produce propagatable depolarization of the AV node and the His bundle. The AH pacing mode may be suitable for patients with varying degrees of heart block or sick sinus syndrome. The HV pacing mode involves sequential pacing of the His bundle and the ventricle. The ventricular pacing may be provided in a demand mode, such that the ventricular pacing pulses are delivered only when the His pacing fails to produce propagatable depolarization of the ventricles. The HV pacing mode may be indicated for patients with persistent or chronic atrial fibrillation, or who have been treated with atrioventricular node ablation or drugs to slow and the rapid ventricular rhythm that often results and allow HBP to predominate. The AHV pacing mode involves sequential atrial, Hisian, and ventricular pacing. One or more of the His-bundle pacing or the ventricular pacing may be delivered in a demand mode. The AHV pacing mode may be indicated for patients with cardiac dyssynchrony and having received cardiac resynchronization therapy, patients suffering from heart failure with left bundle branch block, heart failure induced by right ventricular pacing, long PR intervals with hemodynamic compromise, or pacemaker induced cardiomyopathy from conventional dual-chamber pacing.

Stimulation timing parameters determine the timing and sequence of pacing pulses. For example, in demand AH pacing mode, the HBP pulses are timed relative to an AS or an AP event. An AH timing represents a latency period, within a cardiac cycle, from an intrinsic AS event or an AP event to the delivery of a HBP pulse. In demand HV pacing mode, the ventricular pacing pulses are timed relative to a His pacing event. The HV timing represents a latency period, within a cardiac cycle, from a His bundle event (e.g., a HBP pulse) to the delivery of ventricular pacing pulse. In an example, if a HBP pulse fails to induce ventricular depolarization, a backup ventricular pacing may be delivered at the end of the HV timing. The stimulation timing parameters may additionally include parameters associated with CRT or MSP therapy, such as atrial-ventricular delay (AVD) representing a latency period from an AS or AP event to ventricular pacing, an RV-LV interventricular pacing delay (VVD) representing a time delay between ventricular pacing at the left and right ventricles, or intra-ventricular pacing delay representing a time delay between pacing at multiple site of a ventricle.

The electrostimulation circuit 210 may be configured to provide selective pacing at a site with only a targeted tissue being directly excited, without substantial unintended and undesirable excitation of other non-targeted tissue. If the pacing directly causes intended excitation of the targeted tissue as well as unintended excitation of other non-targeted tissue, a non-selective pacing results. In the context of HBP, selective HBP causes only the excitation (depolarization) of the His bundle, without direct excitation of para-Hisian myocardium adjacent to the His bundle. Non-selective HBP directly causes excitation of both the His bundle and the para-Hisian myocardium. If the HBP pulses cause only excitation of the para-Hisian myocardium or other unintended cardiac tissue, without direct excitation of the His-bundle fibers, then a para-Hisian pacing results. If no tissue excitation is induced by HBP (e.g., neither the para-Hisian myocardium capture nor the His-bundle capture), then a complete loss of capture (LOC) results.

The electrostimulation circuit 210 may be capable of generating backup pacing pulses for delivery to the heart to excite the myocardium and prevent asystole. The backup pacing pulses may be delivered when a loss of capture is produced, or alternatively when para-Hisian capture is produced. The backup pacing may be delivered to a target ventricular site via a lead with associated electrodes disposed in or on a ventricle, such as a right ventricle. Additionally or alternatively, the backup pacing may be delivered to the His bundle, such as the site for delivering HBP pulses, via the same His-bundle pacing lead with associated electrodes. In an example, the backup pacing may include high-output pacing (HOP) pulses with higher pacing energy than conventional pacing pulses. The HOP pulse may be a biphasic or multiphasic waveform. In an example, the HOP pulse may have a peak-to-peak voltage amplitude of 5-8 volts, and a pulse duration of 50-70 msec. With higher amount of energy delivered to the myocardium, the HOP pulse may increase myocardial contractility and improve systolic function. However, chronic HOP pacing may overstress the heart and potentially be hazardous in some heart failure patients. According, in some examples, the HOP pulses may be delivered on an intermittent basis, such that the conventional pacing pulses are delivered in 3-5 cardiac cycles between the HOP pulses. In an example, the HOP pulses may be delivered when one or more physiologic sensors sense a deterioration in cardiac hemodynamics, in addition to the indication of loss of capture of para-Hisian capture. Arcot-Krishnamurthy et al. U.S. Pat. No. 8,588,907, entitled "CLOSED-LOOP CONTROL OF INTERMITTENT EXCITATORY CARDIAC STIMULATION FOR THERAPEUTIC EFFECT," refers to high-output pacing that is excitatory and of sufficient energy to augment myocardial contractility, which is incorporated herein by reference in its entirety.

The sensing circuit 220 may be coupled to one or more electrodes or physiologic sensors to sense a physiologic signal indicative of a response of a portion of the heart 102 to the delivery of HBP pulses. Examples of the sensed signals may include an electrocardiogram (ECG), an electrogram (EGM) of a portion of the heart such as atrial EGM, ventricular EGM, or evoked His potential, an impedance signal, a heart sound signal, or a pressure signal, among other physiological or hemodynamic signals indicative of a tissue response to the delivery of HBP pulses. In an example, the sensing circuit 220 may sense an atrial activation signal 222 indicative of atrial depolarization. In an example, the atrial activation signal 222 may be sensed using the electrode 111 on the lead 106 or atrial electrodes associated with an atrial lead. Alternatively, the atrial activation signal 222 may indicate atrial mechanical activity, which may be sensed using a physiologic sensor.

The atrial activation signal 222 may represent intrinsic atrial activation during normal sinus rhythm (AS) or a response to atrial pacing (AP). In response to HBP, the atrial activation signal 222 may represent atrial retrograde conduction as a result of His-bundle capture. As to be discussed in the following, a capture verification circuit 232, along with the sensing circuit 220, may determine whether the sensed atrial activation 222 is a retrograde atrial conduction as a result of HBP, or an intrinsic AS event or a paced AP event, such as by using timing or signal morphology of the sensed atrial activation 222.

In some examples, portions of the His-bundle pacing system 200 may be implemented distributedly between two devices. In an example, a first device may include the electrostimulation circuit 210 and a stimulation delivery system such as the lead and associated electrodes for delivering the HBP pulses, and a second device may include the sensing circuit 220 and at least a portion of the control circuit 230. The sensing circuit 220 of the second device may be configured to sense, among other signals, the farfield ventricular response to the HBP pulses. In an example, the first and second devices are both implantable devices. In another example, at least one of the first or the second device is a non-implantable, wearable device.

The control circuit 230 may be configured to verify that the HBP pulses capture one or more conductive tissue such as the His bundle or the myocardium, and control the delivery of HBP pulses based on the capture status. In an example, the control circuit 230 can be implemented as a part of a microprocessor circuit in the cardiac disease management system 100. The microprocessor circuit can be a dedicated processor such as a digital signal processor, application specific integrated circuit (ASIC), microprocessor, or other type of processor for processing information including heart sounds. Alternatively, the microprocessor circuit can be a general-purpose processor that can receive and execute instructions of performing the functions, methods, or techniques described herein.

As illustrated in FIG. 2, the control circuit 230 may include circuit sets comprising a capture verification circuit 232, a pacing threshold test circuit 233, and a stimulation control circuit 236. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The capture verification circuit 232 is configured to detect retrograde atrial conduction timing 234 from the sensed atrial activation 222 in response to HBP pulses, and verify the His-bundle capture status based at least on the retrograde atrial conduction timing 234. The present inventor has recognized that a His-bundle capture may result in retrograde atrial conduction closer in time to the HBP pulse, that is, a short His-to-atrial interval (HAI). If HBP fails to capture the His bundle (such as in the case of a LOC, or a para-Hisian capture in which only the para-Hisian myocardium is captured), then retrograde atrial conduction may not be present, or the retrograde atrial conduction may occur but is substantially delayed from the HBP pulse, resulting in a longer HAI. The long AHI during para-Hisian capture may be a result of slow muscle-to-muscle conduction of the activation wavefront that travels from the ventricle to the right atrium via the His bundle as well as the AV node. Additionally, when complete LOC occurs, the atrial activation pattern with respect to HBP pulse (e.g., the 1:1 relationship) may be lost.

Capture verification may be carried out according to a specified schedule, such as on a periodic basis, or continuously on a beat-by-beat basis (i.e., verifying capture in response to each HBP pulse). In an example, the capture verification circuit 232 determines a fast retrograde atrial conduction based on the presence or absence of atrial activation 222 within a specific retrograde conduction detection window $W_{HA}$. Detection of the atrial activation 222 may involve comparing signal strength (e.g., amplitude) of the atrial activation signal 222 to a threshold. The detection window $W_{HA}$ begins at the HBP pulse delivery, and has a specified duration. The duration of $W_{HA}$ may be determined empirically based on measurements of His-to-retrograde atrial conduction intervals in an electrophysiological study, or based on data from a patient population. In an example, the duration of the detection window $W_{HA}$ is approximately 100-225 msec. If the sensing circuit 220 detects the atrial activation 222 within the detection window $W_{HA}$, then a fast retrograde atrial conduction is indicated; and the capture verification circuit 232 decides that His-bundle capture has occurred. If no atrial activation is detected within the detection window $W_{HA}$, then either no retrograde atrial conduction, or a slow retrograde atrial conduction, is indicated; and the capture verification circuit 232 decides that no His-bundle capture has occurred. In another example, the retrograde atrial conduction timing 234 may include a His-to-atrial interval (HAI) between a HBP pulse and the resultant sensed atrial activation 222. The capture verification circuit 232 verifies His-bundle capture if the HAI falls below a HAI threshold ($HAI_{TH}$), or determines a para-Hisian capture or a loss of capture if the HAI exceeds the threshold $HAI_{TH}$. The threshold $HAI_{TH}$ can be determined in a fashion similar to the duration of the retrograde conduction detection window $W_{HA}$ as discussed above. In an example, $HAI_{TH}$ is approximately 100-225 msec. In another example, the capture verification circuit 232 may determine $HAI_{TH}$ using a central tendency of a plurality of HAIs falling within a specific range in response to HBP pulses.

In some patients, para-Hisian capture (i.e., myocardial-only capture without His-bundle capture) may produce slow retrograde atrial conduction that result in atrial activation within the present cardiac cycle and before the next intrinsic atrial activity (e.g., P wave on an ECG, or an AS event). As such, the HAI during LOC may be longer than the HAI during a para-Hisian capture. The capture verification circuit 232 may distinguish para-Hisian capture from LOC using two distinct HAI threshold values $HAI_{TH1} < HAI_{TH2}$, and determines a para-Hisian capture if $HAI_{TH1} < HAI < HAI_{TH2}$, and determines a LOC if $HAI > HAI_{TH2}$. The capture verification circuit 232 may alternatively use distinct post-HBP atrial activity detection windows including a first window $W_{HA1}$ having a window duration equal to $HAI_{TH1}$, and a second window $W_{HA2}$ having a window duration equal to $HAI_{HT2}$. A para-Hisian capture is deemed to have occurred if an atrial activity is detected within $W_{HA2}$ but not in $W_{HA1}$, and a LOC is deemed to have occurred if no atrial activity is detected within $W_{HA2}$. In some examples, the capture verification circuit 232 may distinguish para-Hisian capture from LOC using atrial activation morphology (e.g., P wave morphology), as the LOC would typically result in P waves resumed from sinus rhythm, which can be morphologically distinct from the P waves during para-Hisian capture.

In some examples, His-bundle capture status may be determined additionally or alternatively based on signal morphology of an atrial activation 222. For example, the capture verification circuit 232 may determine a similarity metric between the atrial activation morphology and a morphology template represented by morphological features of a known retrograde atrial activation produced by a known HBP capture, and decides His-bundle capture if the similarity metrics satisfies a specified condition. In some examples, to improve reliability of His-bundle capture status decision, capture verification may be performed for a plurality of HBP pulses delivered over a number of cardiac cycles. A His-bundle capture is determined to have occurred if a substantial amount of the plurality of HBP pulses result in individual His-bundle captures.

Presence of atrial tachyarrhythmia may decrease the reliability of retrograde atrial conduction detection and atrial timing measurement. In an example, the system 200 may include an arrhythmia detector configured to detect a presence or absence of atrial tachyarrhythmia, such as atrial fibrillation or atrial tachycardia. The capture verification circuit 232 may perform His-bundle capture verification only if no atrial tachyarrhythmia is present. The capture verification circuit 232 may additionally check atrial signal quality such as signal-to-noise ratio (SNR) and perform His-bundle capture verification only if the atrial signal quality satisfies a specific condition.

The pacing threshold test circuit 233 may be configured to determine a HBP pacing threshold that represents minimal energy required to produce His-bundle capture. The pacing threshold may be determined during implantation of the IMD 104, and updated periodically at specified time period, or triggered by a specific event, such as when HBP pulses fail to capture the His bundle but instead consistently produce para-Hisian capture or LOC, or by a user command. In some examples, the pacing threshold test circuit 233 may perform HBP threshold testing when the patient is free of atrial arrhythmia, such as atrial fibrillation or atrial tachycardia.

During a threshold test, the electrostimulation circuit 210 may deliver HBP pulses at or near the His bundle in accordance with a threshold test protocol. HBP pulses may be delivered at a rate 10-20 bpm above the measured atrial rate. The threshold test protocol may be machine-readable instructions stored in a memory device, and executable by a machine such as a microprocessor. The instructions specify programming a stimulation parameter to different values and measuring, for each programmed parameter value, a corresponding capture status. In various examples, the stimulation parameter, such as pulse amplitude, may be incremented following a ramp-up protocol, decremented following a ramp-down protocol, or sweep through a set of parameter values such as stored in a storage device. For each stimulation parameter value (e.g., pulse amplitude), the capture verification circuit 232 determines a capture status, such as based on the retrograde atrial conduction timing. As the stimulation parameter value is changed such as according to the threshold test protocol, the pacing threshold test circuit 233 may detect a transition from a first capture status to a second capture status of a different type, and determine a HBP threshold based on that detected transition of capture status. In an example, the pacing threshold test circuit 233 may generate a trend of the retrograde atrial conduction timing, such as a HAI trend, corresponding to multiple descending stimulation strength values in a ramp-down protocol. The pacing threshold test circuit 233 may detect from the HAI trend a prolongation of HAI exceeding a threshold, and determine the HBP threshold using the stimulation strength value corresponding to the detected prolongation of HAI. In another example, the HAI trend may correspond to multiple ascending stimulation strength values in a ramp-up protocol. The pacing threshold test circuit 233 may detect from the HAI trend a shortening of HAI falling below a threshold, and determine the HBP threshold using the stimulation strength value corresponding to the detected shortening of HAI. Examples of the HBP threshold test using a HAI trend are discussed below, such as with reference to FIGS. 3-4.

The stimulation control circuit 236 may include a parameter adjuster circuit 237 configured to determine or update a stimulation parameter value based at least on one or more of the HBP thresholds, such as determined by the pacing threshold test circuit 233. The stimulation parameter may be updated periodically at specified time period, or triggered by a specific event. The stimulation parameter may be updated automatically or manually by a user via a user interface 240. In an example, the parameter adjuster circuit 237 may set the HBP pulse amplitude to the HBP threshold such as determined by the pacing threshold test circuit 233, plus a specified safety margin. The HBP threshold, after being generated, may change over time, such as due to changes in patient pathophysiology, medication, or lead migration or dislodgment. To maintain the desired capture status, the parameter adjuster circuit 237 may dynamically adjust stimulation strength, and the pacing threshold test circuit 233 may accordingly update the HBP threshold.

In addition to the stimulation strength, the parameter adjuster circuit 237 may adjust one or more other stimulation parameters to more effectively activate the His-Purkinje system. In an example, the parameter adjuster circuit 237 may adjust stimulation site, such as by switching to a different stimulation vector configuration including an electrode in close proximity to the His bundle to improve the likelihood of His-bundle capture. In another example, the parameter adjuster circuit 237 may adjust stimulation timing, such as an atrio-Hisian timing relative to an intrinsic or paced atrial event. In yet another example, the parameter adjuster circuit 237 may adjust stimulation mode, such as switching from AH mode to HV mode when a patient develops persistent or chronic atrial fibrillation, or treated with atrioventricular node ablation, or switch from AH pacing mode to AHV mode when the patient develops bundle branch block.

The stimulation control circuit 236 may additionally include a timing circuit 238 configured to time the delivery of the HBP pulses according to a stimulation timing parameter, such as an adjusted stimulation timing provided by the parameter adjuster circuit 237 or programmed by a user via a user interface 240. In an example, the timing circuit 238 may time the delivery of a HBP pulse using an atrio-Hisian (AH) window. The AH window is a programmable latency period with respect to an intrinsic (AS) or paced atrial event (AP). In an example, the AH window may be programmed to approximately 50 msec shorter than a sensed P wave-to-R wave (PR) interval or a programmed atrial-to-ventricular (AV) delay within a cardiac cycle. If an intrinsic His-bundle activity (Hs) is sensed within the AH window, the timing circuit 238 may initiate a His refractory period, during which a HBP pulse may be delivered. In another example, the AH window maybe determined based on an intrinsic AH interval, such that the AH window may be programmed to slightly longer than the intrinsic AH interval (e.g., approximately 1-30 msec longer than the intrinsic AH interval). The HBP would then be timed off of a sensed atrial event but would occur just after the anticipated His event. The delivery of the HBP pulse may trigger a His capture verification window during which an evoked response, such as a FF-QRS or FF-R wave or a hemodynamic signal may be sensed.

Figure 3:
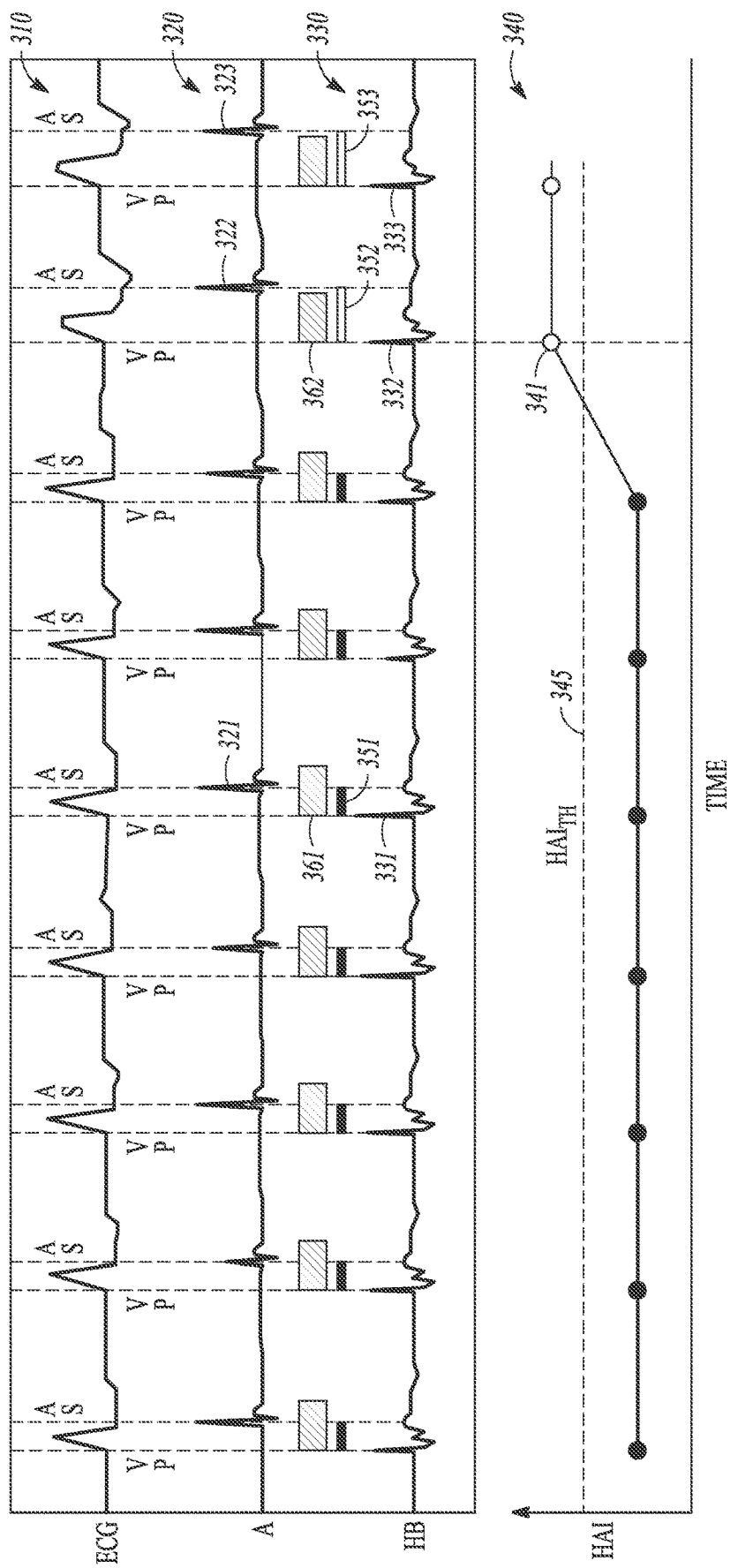
FIG. 3 is a diagram illustrating an example of His-bundle capture verification based on retrograde atrial conduction timing during HBP.
Figure 4:
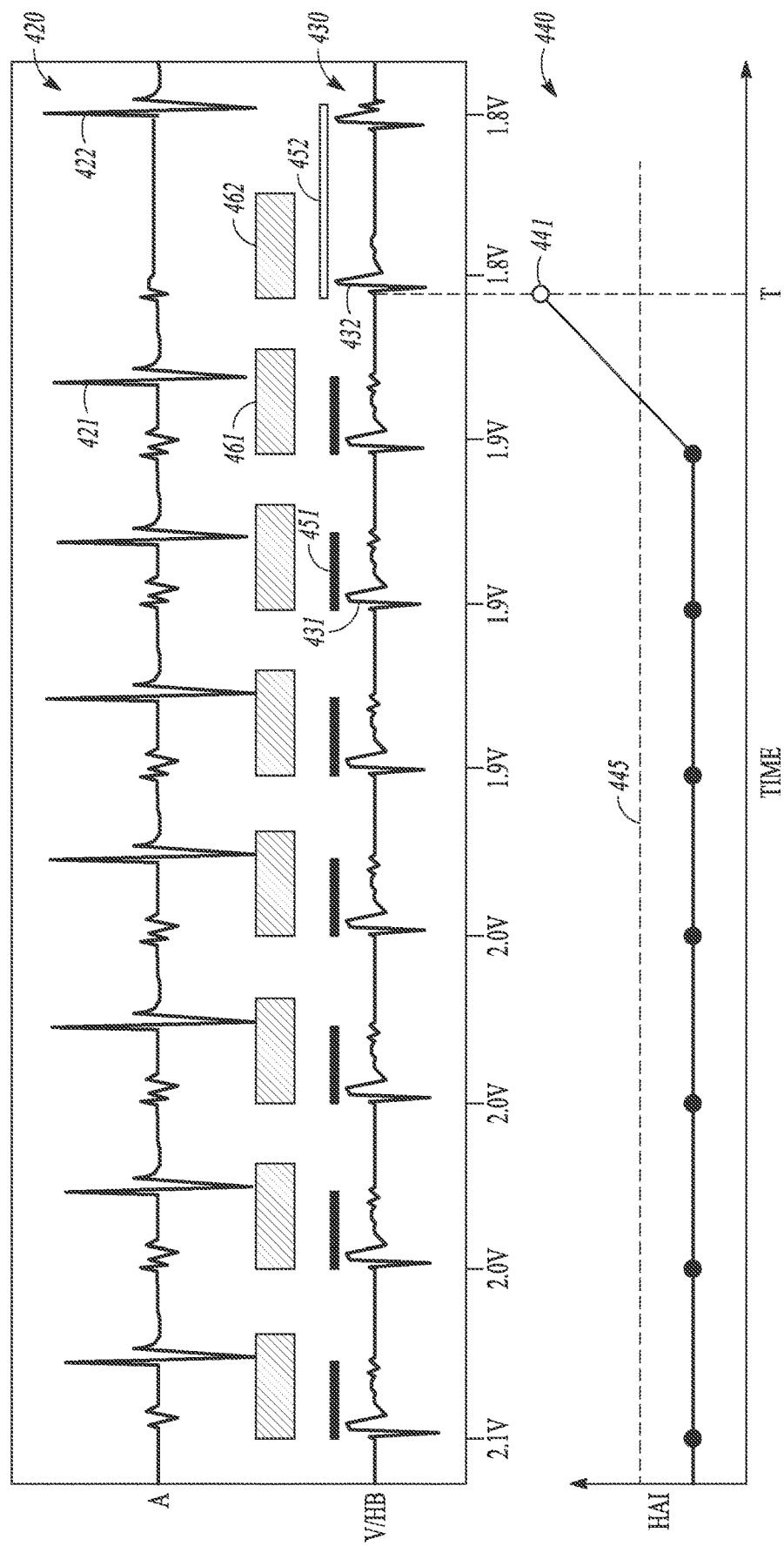
FIG. 4 is a diagram illustrating an example of HBP threshold test based on capture status at various pacing amplitudes.

The user interface 240 may include an input unit and an output unit. In an example, at least a portion of the user interface 240 may be implemented in the external system 140. The input unit may receive user input such as values of the parameters for physiologic event sensing, and His bundle response and myocardial response detections. The user input may receive user programming of stimulation parameters, or confirmation, rejection, or otherwise modification of the stimulation parameters generated by the parameter adjuster circuit 237. The input unit may include an input device such as a keyboard, on-screen keyboard, mouse, trackball, touchpad, touch-screen, or other pointing or navigating devices. The output unit may include circuitry configured to generate a human-perceptible notification of His-bundle capture status and/or various HBP thresholds. The output circuit may be coupled to a display for displaying the received physiologic signals, including tracings of one or more of atrial EGM, His-bundle EGM, ventricular EGM, surface electrocardiogram, or other sensor signals. The display may also display event sensing information such as intrinsic depolarizations, paced events (such as HBP pulses), and timing information on each of the sensed signals. The event sensing information may be overlaid with the signal tracings, or be displayed in a separate marker channel. The stimulation parameters, and intermediate measurements or computations may also be displayed. In an example, the output circuit may generate a trend of the retrograde atrial conduction timing over time, such as a HAI trend corresponding to multiple HBP pulses. The trend may be generated during HBP delivery, or during a HBP threshold test where the HAI values correspond to distinct stimulation strength values. The trend may be displayed to a user to help the user to make programming changes to HBP therapy. Examples of the HAI trend during HBP or during pacing threshold test are illustrated in FIGS. 3 and 4. The output circuit 230 may be coupled to a printer for printing hard copies of information about the event detection and therapy titration protocol. The information may be presented in a table, a chart, a diagram, or any other types of textual, tabular, or graphical presentation formats. The presentation of the output information may include audio or other media formats. In an example, the output unit may generate alerts, alarms, emergency calls, or other forms of warnings to signal the system user about the His-bundle capture status. In an example, the output unit may generate an alert when a loss of capture is indicated and a backup pacing is delivered. In another example, frequent backup pacing delivery may trigger the output unit to generate an alert and prompt a user (e.g., a clinician) to reprogram the pacing system.

FIG. 3 is a diagram illustrating an example of His-bundle capture verification based on retrograde atrial conduction timing during HBP. By way of example and not limitation, the cardiac electrical signals include an ECG 310, an intracardiac atrial EGM 320, and a His-bundle EGM 330. The signals 310-330 may be concurrently recorded from a patient, such as by using the sensing circuit 220. HBP pulses may be delivered, such as by using the electrostimulation circuit 210, at a rate faster than patient intrinsic sinus rate. In an example, the HBP pulses are delivered at 10-20 bpm above the intrinsic sinus rate to promote the occurrence of retrograde atrial activation. Following the delivery a HBP pulse, an atrial activation may be detected from the atrial EGM 320. Retrograde atrial conduction timing, such as a His-to-atrial intervals (HAI) corresponding to the HBP pulses, may be measured. By way of example, following a HBP pulse 331, a retrograde atrial activity 321 can be detected from the atrial EGM 320, and a corresponding HAI 351 may be measured as a time interval between the HBP pulse 331 and the retrograde atrial activity 321.

Also shown in FIG. 3 is a HAI trend 340 representing HAI values corresponding to a train of HBP pulses. Prior to time T, HAI values are short and below a HAI threshold ($HAI_{TH}$) 345, indicating fast retrograde conduction. At time T, the HBP pulse 332 results in a delayed retrograde atrial activity 322. The corresponding HAI 352 is substantially longer than previous HAI values (e.g., the HAI 351), and exceeds the threshold $HAI_{TH}$ 345. The long HAI 352 indicate a slow retrograde conduction. The capture verification circuit 232 may determine that the HBP pulses prior to T capture the His bundle, while the HBP pulse 332 fails to capture the His bundle due to the slow retrograde conduction as indicated by the long HAI 352. Subsequent HBP pulse 333 results in a HAI 353, which exceeds the threshold $HAI_{TH}$ 345, indicating slowly conducted atrial retrograde activity 323. As such, the HBP pulse 333 also fails to capture the His bundle.

FIG. 3 also illustrate a series of detection windows WHA immediately following the corresponding HBP pulses. The capture verification circuit 232 may alternatively or additionally detects retrograde atrial conduction from the atrial EGM 320 using the detection windows $W_{HA}$. The duration of $W_{HA}$ may take a value equal to $HAI_{TH}$, which can be determined empirically based on His-to-atrial retrograde conduction timing. In an example, the duration of $W_{HA}$ may be pre-determined to be approximately 100-225 msec. As illustrated in FIG. 3, prior to time T, atrial activations are detected within corresponding $W_{HA}$ following the HBP pulses (e.g., atrial event 321 is detected within $W_{HA}$ 361). At time T, the delayed atrial activity 322 is not detected within the corresponding $W_{HA}$ 362. Based on the presence or absence of atrial activity within $W_{HA}$, the capture verification circuit 232 may determine the HBP pulses prior to time T have captured the His bundle, while the HBP pulses 332 and 333 fail to capture the His bundle.

The capture verification circuit 232 may alternatively or additionally determine a change of HAI trend, such as a change from a baseline HAI that may be determined using a moving average of the HAI values that fall within a specified range. A prolonged HAI may indicate a transition from His-bundle capture to LOC or para-Hisian capture. In the example as illustrated in FIG. 3, the HAI transition 341 from a short to long HAI, when exceeding a threshold value $HAI_{TH}$, may indicate an occurrence of LOC or para-Hisian capture. In some examples, the degree of HAI prolongation at the HAI transition, such as a difference between the HAI at time T and the previous HAI or an established baseline HAI, may be compared to a prolongation threshold to determine an occurrence of para-Hisian capture or a complete LOC. An example of the prolongation threshold is approximately 50-75 msec. In some examples, LOC or para-Hisian capture may be confirmed such as by a consecutive of long HAIs (i.e., exceeding the $HAI_{TH}$), or a substantially number of long HAIs within a time period of a specified number of HBP pulses. The stimulation control circuit 236 may adjust one or more pacing parameters such as pacing amplitude, pacing frequency, pulse width, or duty cycle, to improve His-bundle capture. Additionally or alternatively, the stimulation control circuit 236 may initiate a HBP threshold test to determine a new HBP threshold.

FIG. 4 is a diagram illustrating an example of HBP threshold test based on capture status at various pacing amplitudes. In the illustrated example, an intracardiac atrial EGM 420 and a His-bundle EGM 430 are concurrently recorded from a patient during a HBP threshold test. The HBP threshold test can be performed using the pacing threshold test circuit 233 in accordance with a ramp-down protocol, which includes descending HBP stimulation amplitudes of 2.1V, 2.0V, 1.9V, and 1.8V, etc., as illustrated in FIG. 4. Similar to FIG. 3, HBP pulses may be delivered at a rate faster than patient intrinsic sinus rate. Atrial activities are detected from the atrial EGM 420, and HAIs are determined for each HBP pulse at corresponding pacing amplitude. As illustrated in FIG. 4, HAIs corresponding to HBP pulses with pacing amplitudes of 2.1V, 2.0V, and 1.9V are short, as they all fall below the threshold $HAI_{TH}$ 445, indicating a fast retrograde conduction and His-bundle capture. For example, HBP pulse 431 with a pacing amplitude of 1.9V captures the His bundle. Through fast retrograde conduction, it generates an atrial activity 421 with a relatively short HAI 451 falling below the threshold $HAI_{TH}$ 445. When the pacing amplitude is decreased to 1.8V at time T, the HBP pulse 432 does not produce a fast conducted retrograde atrial activity. The next atrial activity 422 following the HBP pulse 432 is an intrinsic atrial activation (P wave, or AS event on the atrial EGM 420). The HAI 452, corresponding to the HBP pulse 432, is longer than the threshold $HAI_{TH}$ 445. The HAI transition 441 from a short HAI to a long HAI, when exceeding a threshold value $HAI_{TH}$, indicates that the HBP pulse 432 does not capture the His bundle, with or without para-Hisian myocardial capture. That is, the HBP pulse 432 results in a para-Hisian capture, or a complete LOC. In some examples, the degree of HAI prolongation at the HAI transition, such as a difference between the HAI at time T and the previous HAI or an established baseline HAI, may be compared to a prolongation threshold to determine an occurrence of para-Hisian capture or a complete LOC. An example of the prolongation threshold is approximately 50-75 msec. The pacing threshold test circuit 233 may then determine the HBP threshold to be approximately 1.9V, representing a minimum stimulation strength required to produce His-bundle capture. A safety margin may be added to the determined HBP threshold to improve the probability of His bundle capture.

The capture verification during the pacing threshold test may alternatively or additionally be based on a HAI trend 440 similar to the HAI trend 340 as illustrated in FIG. 3. A substantial deviation (e.g., exceeding a threshold value) from the HAI trend, such as the HAI transition 351 from a short to long HAI, when exceeding a threshold value, may indicate that the HBP pulse at the corresponding pacing amplitude fails to produce His-bundle capture. Additionally or alternatively, the capture verification during the pacing threshold test may be based on atrial activity detection within the detection window $W_{HA}$ as discussed above with reference to FIG. 3. For example, the atrial activity 421 may be detected within the window 461 that starts immediately following the HBP pulse 431, indicating a successful His-bundle capture at the corresponding pacing amplitude of 1.9V. When the pacing amplitude is decreased to 1.8V, no atrial activity is detected with the window 462 following the HBP pulse 432, indicating no His-bundle capture has occurred. The HBP threshold may then be determined to be 1.9V.

Figure 5:
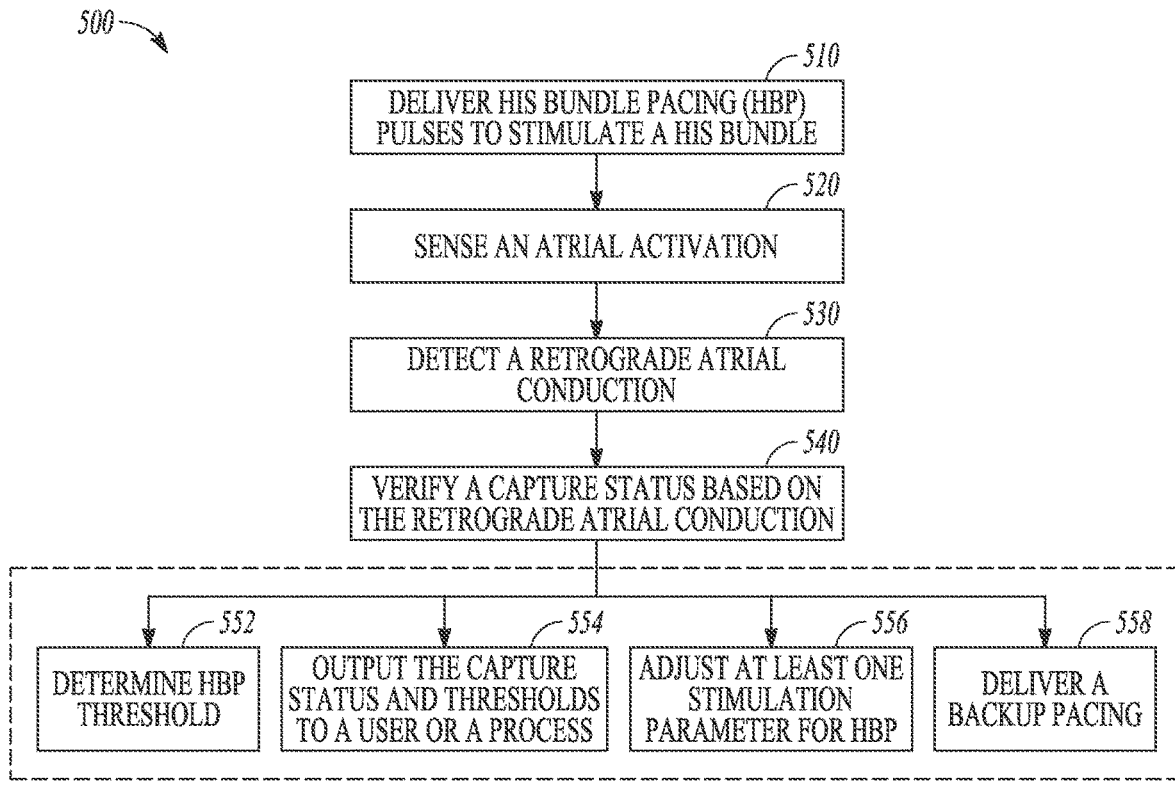
FIG. 5 is a flowchart illustrating generally an example of a method 500 for providing HBP to a patient using a medical system.

FIG. 5 is a flowchart illustrating generally an example of a method 500 for providing His-bundle pacing (HBP) to a patient using a medical system. The method 500 may be implemented and executed in an ambulatory medical device such as an implantable or wearable medical device, or in a remote patient management system. In an example, the method 500 may be implemented in, and executed by, the IMD 104, one or more devices in the external system 140, or the His-bundle pacing system 200.

The method 500 commences at 510, where HBP pulses may be generated and delivered to a target site to stimulate the His bundle of the patient heart. The target site may include a region at or near the His bundle 121, such as a region distal to the blocked or slowly conducting AV node and in the AV septum, an interventricular septum region, or a right atrial region near the His-bundle 121. The HBP pulse may be generated by the electrostimulation circuit 210, according to programmed stimulation parameters. Examples of the stimulation parameters may include stimulation site, stimulation mode, stimulation timing, or stimulation strength, among other parameters. The stimulation strength parameters determine the amount of energy delivered to the pacing site, and may include pulse amplitude, pulse width, pulse frequency, pulse waveform, duty cycle, or stimulation duration. In an example, the HBP pulses may be programmed with different stimulation strength values, such as pulse amplitudes. The HBP pulses may be delivered via a delivery system including, for example, the lead 106 and one or more of the electrodes 112A-112B. In an example, HBP pulses may be delivered in multiple cardiac cycles, such that at least one pulse is delivered within each of the multiple cardiac cycles.

At 520, an atrial activation signal may be sensed in response to the HBP pulses, such as using the sensing circuit 220. The atrial activation signal may include an intra-atrial EGM sensed from the left or right atrium, P-waves as detected from an ECG signal, or sensor signals indicative of atrial mechanical contraction. Examples of atrial mechanical signal may include impedance signal, heart sounds signal, or cardiac pressure signals, among others. The atrial activation signal may represent intrinsic atrial activation during normal sinus rhythm (AS) or a response to atrial pacing (AP).

At 530, a retrograde atrial conduction may be detected using the sensed atrial activation. The retrograde atrial conduction may be detected based on the presence or absence of the atrial activation within a specific retrograde conduction detection window $W_{HA}$. The detection window $W_{HA}$ begins at the HBP pulse delivery, and has a specified duration, which is approximately 100-225 msec in an example. His-bundle capture status may be verified at 540 using the detected retrograde atrial conduction. A capture status represents types of tissue (e.g., His-bundle fibers, or myocardium at the stimulation site) directly activated by the HBP pulses and the manners of activation. The capture status may be verified on a beat-by-beat basis over multiple cardiac cycles. If an atrial activation is sensed within the detection window $W_{HA}$, a fast retrograde atrial conduction is indicated, then at 540 a His-bundle capture is verified. However, if no atrial activation is detected within the detection window $W_{HA}$, it indicates that either no retrograde atrial conduction, or a slow retrograde atrial conduction has occurred; then at 540, no His-bundle capture has occurred.

In another example, a retrograde atrial conduction may be detected using a His-to-atrial interval (HAI) between a HBP pulse and the resultant sensed atrial activation. A His-bundle capture may generally result in retrograde atrial conduction closer in time to the HBP pulse, that is, a short His-to-atrial interval (HAI). If HBP fails to capture the His bundle (such as in the case of a LOC, or a para-Hisian capture where only para-Hisian myocardium is captured), retrograde atrial conduction may not present, or can significantly delayed from the HBP pulse due to slow muscle-to-muscle conduction of the activation wavefront traveling from the ventricle to the right atrium via the His bundle as well as the AV node. This may result in a long HAI. His-bundle capture may be verified if the HAI falls below a HAI threshold ($HAI_{TH}$); and a para-Hisian capture or a loss of capture is determined if the HAI exceeds the threshold $HAI_{TH}$. The threshold $HAI_{TH}$ can be determined in a fashion similar to the duration of the retrograde conduction detection window $W_{HA}$ as discussed above. In an example, the threshold value is approximately 100-225 msec. In another example, the threshold value may be determined using a central tendency of a plurality of HAIs falling within a specific range in response to HBP pulses.

His-bundle capture status may be verified additionally or alternatively based on signal morphology of the atrial activation sensed at 520. A similarity metric between the atrial activation morphology and a morphology template, such as represented by morphological features of a known retrograde atrial activation produced by a known HBP capture, may be computed. At 540, a His-bundle capture is deemed to have occurred if the similarity metric satisfies a specified condition, such as exceeding a threshold or falling in a specific value range.

In some examples, cardiac arrhythmias may be detected at 520 such as by using the sensed atrial activation. Presence of atrial tachyarrhythmia may decrease the reliability of retrograde atrial conduction detection at 530 and thus the timing of atrial activation. His-bundle capture verification at 540 may be performed only if no atrial tachyarrhythmia is present.

In some examples, capture verification at 540 may include distinguishing para-Hisian capture from LOC, such as by using two distinct HAI threshold values $HAI_{TH1} < HAI_{TH2}$. A para-Hisian capture is detected if $HAI_{TH1} < HAI < HAI_{TH2}$, and a LOC is detected if $HAI > HAI_{TH2}$. Alternatively, distinct post-HBP atrial activity detection windows, including a first window $W_{HA1}$ having a window duration equal to $HAI_{TH1}$, and a second window $W_{HA2}$ having a window duration equal to $HAI_{HT2}$, may be used to distinguish para-Hisian capture from LOC. A para-Hisian capture is detected if an atrial activity is detected within $W_{HA2}$ but not in $W_{HA1}$, and a LOC is detected if no atrial activity is not detected within $W_{HA2}$.

The His-bundle capture status as verified at 540 may be used output to one or more diagnostic or therapeutic processes. In one example, a HBP threshold may be determined at 552, such as by using the pacing threshold test circuit 233. The HBP threshold may be determined during implantation of the IMD 104, and updated periodically at specified time period, or triggered by a specific event, such as when HBP pulses fail to capture the His bundle but instead consistently produce para-Hisian capture or LOC, or by a user command. During the threshold test, stimulation parameter, such as pulse amplitude, may be incremented following a ramp-up protocol, decremented following a ramp-down protocol, or sweep through a set of stored parameter values. Capture status may be verified at each pacing parameter value, such as based on the retrograde atrial conduction timing. A HBP threshold may be determined at 552 based on a prolongation of HAI exceeding a threshold during a ramp-down protocol with descending stimulation amplitudes, or based on a shortening of HAI falling below a threshold in a ramp-up protocol with ascending stimulation amplitudes, as discussed above reference to FIGS. 3-4.

At 554, the His-bundle capture status, and optionally the HBP threshold, may be output to a user (e.g., a clinician) or a process at 552, such as being displayed on a display of the user interface 240. The HAI trend, along with the sensed physiologic signals, such as those illustrated in FIG. 3 or 4, or the programmed stimulation parameters, among other intermediate measurements or computations, may also be displayed.

Additionally or alternatively, at 556, one or more stimulation parameters may be adjusted based on the capture status at 540 and optionally the HBP threshold determined at 552. such as via the parameter adjuster circuit 237. The parameter adjustment may include switching to a different stimulation site, using a different pacing vector configuration, adjusting timing of HBP pulses with respect to an intrinsic or paced atrial activation, adjusting stimulation strength such as one or more of pulse amplitude, pulse width, pulse frequency, pulse waveform, duty cycle, or stimulation duration. In some examples, stimulation parameter adjustment may be based on capture statistics computed using the capture verification and classification results over multiple heart beats. Examples of the capture statistics may include percentages, histograms, or other measures of distribution of the selective His-bundle capture, non-selective His-bundle capture, or para-Hisian capture. In some examples, the HBP pulse amplitude to the HBP threshold such as determined by the pacing threshold test circuit 233, plus a specified safety margin.

At 558, a backup pacing may be delivered when certain capture status results, such as a LOC, or a para-Hisian capture. The backup pacing may be delivered to a target ventricular site via a lead with associated electrodes disposed in or on a ventricle, such as a right ventricle. Additionally or alternatively, the backup pacing may be delivered at or near the His bundle. In an example, the backup pacing pulses include high-output pacing (HOP) pulses with higher pacing energy than conventional pacing pulses. In some examples, the HOP pulses may be delivered on an intermittent basis, such that the conventional pacing pulses are delivered in 3-5 cardiac cycles between the HOP pulses. In addition to backup ventricular pacing, other therapies, such as CRT, BiV pacing, LV-only pacing, single site LV pacing, or multi-site LV pacing may be delivered to improve myocardial contractility and cardiac performance.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:
1. A system for pacing a heart, comprising:
   an electrostimulation circuit configured to generate His-bundle pacing (HBP) pulses at a pulse rate higher than an intrinsic heart rate to stimulate a His bundle of the heart;

a sensing circuit configured to sense an atrial activation of the heart; and a control circuit, including a capture verification circuit configured to:

generate a His-to-atrial interval (HAI) trend over time, the HAI trend comprising HAIs each representing respective intervals between the HBP pulses and atrial activations in response to the respective HBP pulses;

detect a retrograde atrial conduction based on a change in the HAI trend; and verify a His-bundle capture status based at least on the detected retrograde atrial conduction.

2. The system of claim 1, wherein the sensing circuit is configured to sense the atrial activation during an atrial detection window ($W_{HA}$) following the HBP pulse, and the capture verification circuit is configured to verify the His-bundle capture status as one of:

a His-bundle capture if the atrial activation is detected within the $W_{HA}$; or a para-Hisian capture or a loss of capture if no atrial activation is detected within the $W_{HA}$.

3. The system of claim 1, wherein the capture verification circuit is configured to verify the His-bundle capture status as one of:

a His-bundle capture if the HAI falls below a threshold value; or a para-Hisian capture or a loss of capture if the HAI exceeds the threshold value.

4. The system of claim 3, wherein the capture verification circuit is configured to generate the threshold value using a central tendency of a plurality of HAIs falling within a specific range in response to HBP pulses.

5. The system of claim 1, wherein the control circuit includes a pacing threshold test circuit coupled to the capture verification circuit, wherein:

the capture verification circuit is configured to verify His-bundle capture status in response to HBP pulses having multiple stimulation strength values in accordance with a threshold test protocol; and the pacing threshold test circuit is configured to determine, using the verified capture status, a HBP threshold.

6. The system of claim 5, wherein the threshold test protocol includes a stimulation strength ramp-down protocol, and the pacing threshold test circuit is configured to determine the HBP threshold corresponding to a prolongation of HAI exceeding a threshold.

7. The system of claim 5, wherein the threshold test protocol includes a stimulation strength ramp-up protocol, and the pacing threshold test circuit is configured to determine the HBP threshold corresponding to a shortening of HAI falling below a threshold.

8. The system of claim 5, wherein the pacing threshold test circuit is configured to determine or update the HBP threshold in response to a para-Hisian capture or a loss of capture.

9. The system of claim 1, further comprising an arrhythmia detector configured to detect a presence or absence of atrial tachyarrhythmia, wherein the capture verification circuit is configured to verify the His-bundle capture status in the absence of the atrial tachyarrhythmia.

10. The system of claim 9, where the control circuit includes a pacing threshold test circuit configured to determine a HBP threshold in response in the absence of the atrial tachyarrhythmia.

11. The system of claim 1, wherein the control circuit is configured adjust a stimulation parameter of HBP based on the verified His-bundle capture status.

12. A method for operating a pacing system to stimulate a heart, the method comprising:

generating His-bundle pacing (HBP) pulses at a pulse rate higher than an intrinsic heart rate to stimulate a His bundle of the heart using an electrostimulation circuit;

sensing an atrial activation of the heart using sensing circuit;

generating, via a control circuit, a His-to-atrial interval (HAI) trend over time, the HAI trend comprising HAIs each representing respective intervals between the HBP pulses and atrial activations in response to the respective HBP pulses;

detecting, via the control circuit, a retrograde atrial conduction based on a change in the HAI trend; and verifying, via the control circuit, a capture status based at least on the detected retrograde atrial conduction.

13. The method of claim 12, wherein:

sensing the atrial activation is performed during an atrial detection window ($W_{HA}$) following the HBP pulse; and verifying the capture status includes recognizing a His-bundle capture if the atrial activation is detected within the $W_{HA}$, or a para-Hisian capture or a loss of capture if no atrial activation is detected within the $W_{HA}$.

14. The method of claim 12, wherein verifying the capture status includes recognizing a His-bundle capture if the HAI falls below a threshold value, or a para-Hisian capture or a loss of capture if the HAI exceeds the threshold value.

15. The method of claim 14, comprising:

varying stimulation strength of the HBP pulses and verifying His-bundle capture status in response to HBP under the varied stimulation strength; and determining a HBP threshold using the verified His-bundle capture status under the varied stimulation strength.

16. The method of claim 15, wherein:

varying the stimulation strength of the HBP pulses includes ramping down the stimulation strength; and determining the HBP threshold corresponds to a prolongation of HAI exceeding a threshold.

17. The method of claim 15, wherein:

varying the stimulation strength of the HBP pulses includes ramping up the stimulation strength; and determining the HBP threshold corresponds to a shortening of HAI falling below a threshold.

18. The method of claim 12, comprising detecting a presence or absence of atrial tachyarrhythmia, and wherein verifying the capture status is performed in the absence of the detection of atrial tachyarrhythmia.

19. The system of claim 1, wherein the change in the HAI trend includes a HAI difference between a first HAI and a baseline HAI or a second HAI preceding the first HAI, and wherein the capture verification circuit is configured to detect a transition from a His-bundle capture to a loss of capture or a para-Hisian capture based on the HAI difference.

20. The method of claim 12, wherein the change in the HAI trend includes a HAI difference between a first HAI and a baseline HAI or a second HAI preceding the first HAI, and wherein verifying the capture status includes detecting a transition from a His-bundle capture to a loss of capture or a para-Hisian capture based on the HAI difference.

* * * * *